United States Patent
Boussand et al.

(10) Patent No.: US 7,176,338 B2
(45) Date of Patent: Feb. 13, 2007

(54) PROCESS FOR PREPARING 1,1,1-TRIFLUORO-2, 2-DICHLOROETHANE

(75) Inventors: Béatrice Boussand, Sainte Foy les Lyon (FR); Eric Jorda, Lyons (FR)

(73) Assignee: Atofina, Puteaux (FR)

( * ) Notice: Subject to any disclaimer, the term of this patent is extended or adjusted under 35 U.S.C. 154(b) by 482 days.

(21) Appl. No.: 10/814,162

(22) Filed: Apr. 1, 2004

(65) Prior Publication Data

US 2004/0186327 A1    Sep. 23, 2004

Related U.S. Application Data

(62) Division of application No. 10/210,814, filed on Aug. 2, 2002, now Pat. No. 7,053,252.

(30) Foreign Application Priority Data

Aug. 3, 2001 (FR) ..................... 1/10451

(51) Int. Cl.
C07C 17/20 (2006.01)
C07C 17/093 (2006.01)

(52) U.S. Cl. ..................... 570/168; 570/164; 570/165; 570/166

(58) Field of Classification Search ................ 570/168, 570/164, 165, 166
See application file for complete search history.

(56) References Cited

U.S. PATENT DOCUMENTS

| | | | |
|---|---|---|---|
| 3,787,331 A | 1/1974 | Groppelli et al. | |
| 3,793,229 A | 2/1974 | Groppelli et al. | |
| 4,145,368 A | 3/1979 | Sweeney et al. | |
| 4,147,733 A | 4/1979 | Fiske et al. | |
| 4,192,822 A | 3/1980 | Sweeney et al. | |
| 5,091,601 A | 2/1992 | Carmello et al. | |
| 5,262,574 A | 11/1993 | Carmello et al. | |
| 5,414,166 A | 5/1995 | Kim et al. | |
| 5,723,700 A | 3/1998 | Lee et al. | |

FOREIGN PATENT DOCUMENTS

| | | |
|---|---|---|
| EP | 0 346 612 | 12/1989 |
| EP | 0 402 874 | 12/1990 |
| EP | 0 407 990 | 1/1991 |
| EP | 0 456 552 | 11/1991 |
| EP | 0 462 514 | 12/1991 |
| EP | 0 486 333 | 5/1992 |
| EP | 0 502 605 | 9/1992 |
| EP | 0 526 908 | 2/1993 |
| EP | 0 583 703 | 2/1994 |
| EP | 0 609 124 | 8/1994 |
| EP | 0 638 535 | 2/1995 |
| FR | 2 669 022 | 5/1992 |
| FR | 2 758 137 | 7/1998 |
| WO | WO 94/11327 | 5/1994 |
| WO | WO 95/16654 | 6/1995 |
| WO | WO 95/21147 | 8/1995 |
| WO | WO 93/16798 | 9/2003 |

OTHER PUBLICATIONS

McBee et al., "Fluorinated Derivatives of Ethane", Ind. Eng. Chem. 39, pp. 409-412, dated Mar. 1947.

*Primary Examiner*—Elvis O. Price
(74) *Attorney, Agent, or Firm*—Smith, Gambrell & Russell, LLP

(57) ABSTRACT

The invention relates to a process for preparing 1,1,1-trifluoro-2,2-dichloroethane (F123).

This process consists in placing 1,1,1-trifluoro-2-chloroethane (F133$a$) in contact with chlorine in the presence of hydrogen fluoride and a fluorination catalyst.

F133$a$ may be obtained by fluorination of trichloroethylene, and the F123 may be subsequently fluorinated to F125.

3 Claims, 2 Drawing Sheets

PROCESS FOR PREPARING 1,1,1-TRIFLUORO-2, 2-DICHLOROETHANE

CROSS REFERENCE TO RELATED APPLICATION

This application is a division of Ser. No. 10/210,814, filed Aug. 2, 2002, now U.S. Pat. No. 7,053,252 and which is incorporated in its entirety herein by reference.

FIELD OF THE INVENTION

The present invention relates to a process for preparing 1,1,1-trifluoro-2,2-dichloroethane (F123) by catalytic chlorination of 1,1,1-trifluoro-2-chloroethane (F133a) in the presence of hydrogen fluoride (HF). The invention also relates to the application of this process to a process for manufacturing pentafluoroethane (F125).

BACKGROUND OF THE INVENTION

Since the compounds F123 and F125 may be used as substitutes for perchlorofluorocarbons (CFCs) in the field of aerosols (propellants) and in the field of refrigeration, efficient processes for their industrial production are currently being sought.

WO 95/16654 describes the placing in contact, at a temperature of 340° C., of F133a with chlorine and HF in the presence of a chromium catalyst. Although the conversion of the F133a in this reaction is high, it mainly produces 1,1,1,2-tetrafluoroethane (F134a) at this temperature. Thus, the selectivity towards F123 does not exceed 15%, which does not allow a production of this compound under industrially acceptable conditions to be envisaged.

WO 94/11327 mentions the placing in contact, at temperatures below 300° C., of F133a with chlorine and HF in the presence of a chromium catalyst. This reaction is carried out with a very large excess of chlorine and HF, and preferentially leads to the formation of F124 and F125; thus, the selectivity towards F123 remains less than 8% and the 110 series/120 series ratio is greater than 10%.

EP-A-526 908 and EP-A-346 612 propose the preparation of F123 by placing chlorine in contact with F133a, at a temperature preferably between 350 and 450° C., in the presence or absence of a catalyst, this chlorination being carried out in the absence of HF.

U.S. Pat. No. 4,145,368 proposes a process that consists in reacting chlorine with F133a, then separating the F123 from the reaction medium, and reacting the F113a resulting from this separation with a further amount of F133a, this reaction being carried out in the vapour phase and preferably between 350 and 425° C., in the presence of a catalyst such as a chromium oxide.

According to the said document, the final selectivity towards F123 does not exceed 29%.

EP-B-407 990 proposes the chlorination of F133a to F123 by thermal or catalytic activation, in the liquid phase under pressure. The selectivity towards F123 may range from 67.9 to 83.4%, the reaction pressure ranging from 50 to 127 bar.

EP-A-402 874 proposes to react chlorine with F133a between 350 and 450° C., in the absence of a catalyst and of HF. According to the said document, the production of F113a may be eliminated by means of a particular combination of temperature conditions, contact time and molar ratio of reagents.

U.S. Pat. No. 5,414,166 proposes a chlorination of F133a in the presence of hydrogen, between 250 and 500° C. and preferably between 350 and 450° C.: the selectivity towards F123 may range from 65% to 92%.

U.S. Pat. No. 5,723,700 describes a step during which F133a, HF and $Cl_2$ react, in the presence of a fluorination catalyst, between 300 and 450° C. to give essentially F134a and traces of F123.

DETAILED DESCRIPTION OF THE INVENTION

The aim of the invention is to propose a process for preparing F123 by chlorination of F133a, giving an improved conversion of F133a and/or an improved selectivity towards F123.

The aim of the invention is also to propose a process for preparing F123 by chlorination of F133a, which may be carried out at a relatively moderate temperature.

Another aim of the invention is to propose a process for preparing F123 by chlorination of F133a, which may be carried out at atmospheric pressure or under moderate pressure, for example not exceeding 25 bar.

Another aim of the invention is to propose a process for preparing F123 by chlorination of F133a, giving rise to a selectivity towards F123 of greater than 90%.

Another aim of the invention is to propose yet another such process, giving rise to a selectivity towards F123 of greater than 95%.

It has now been found that at least one of the abovementioned aims is achieved by means of the process described below.

One subject of the present invention is thus a process for preparing 1,1,1-trifluoro-2,2-dichloroethane (F123) by placing 1,1,1-trifluoro-2-chloroethane (F133a) in contact with chlorine, the said process being characterized in that the said placing in contact is performed:

in the presence of HF;
under temperature conditions, with a contact time and with $Cl_2$/F133a and HF/F133a molar ratios such that HF substantially does not react with the F133a and the F123 formed, and promotes the selectivity towards F123; and
in the presence of a bulk catalyst consisting of aluminum fluoride or of a mixture of aluminum fluoride and alumina, or of a catalyst based on iron, or on iron and nickel, supported on aluminum fluoride or on a mixture of aluminum fluoride and alumina.

The invention relates more particularly to a process such that HF does not react substantially with F133a and F123 to give derivatives that are more fluorinated than F133a, such as F124 or F134a.

In carrying out the process according to the invention, operating conditions should be selected such that HF behaves essentially as a diluent and/or stabilizer for the reaction and the reagents, rather than as a reagent in a fluorination reaction. In general, the temperature conditions, the $Cl_2$/F133a and HF/F133a molar ratios and the contact time may be chosen within known ranges for this type of chlorination reaction and, for example, as reported above with reference to the documents relating to the said chlorination reaction.

For purely illustrative purposes, which consequently cannot limit the field of the invention, recommended orders of magnitude for the operating conditions under consideration will be given below.

In general, the temperature of the reaction medium is between 150 and 320° C. This temperature is preferably between 250 and 300° C.

The chlorine/F133a molar ratio may be between 0.01 and 0.50 and is preferably between 0.1 and 0.3.

The HF/F133a molar ratio can generally be between 0.5 and 2.5. For practical reasons associated, inter alia, with the separation of the products for the purpose of recycling the unconsumed reagents, and the HF, a ratio of between 0.8 and 1.2 is preferably chosen.

The contact time between F133a, chlorine and HF on the catalyst may be between 5 and 100 seconds; it is recommended to have a contact time of between 10 and 60 seconds. The contact time herein is calculated as the ratio of the apparent volume of the catalyst to the total volume flow rate of gases fed into the reactor, under the reaction pressure and temperature conditions.

The catalyst that may be used for this invention is a catalyst consisting of aluminum fluoride or a mixture of aluminum fluoride and alumina, onto which are optionally deposited oxides, halides and/or oxyhalides of iron, or else of iron and nickel. Catalysts consisting of aluminum fluoride, alone or as a mixture with alumina, are described especially in EP 0 609 124. Catalysts based on iron, or on iron and nickel, are prepared by dry-impregnating aluminum fluoride or a mixture of aluminum fluoride and alumina, either by a solution of ferric chloride, or by a solution containing a mixture of nickel chloride and ferric chloride. The impregnation is followed by a step of drying under nitrogen.

When an iron-based catalyst is used, the iron content is generally less than 30% by weight and is preferably less than 15%. When a catalyst based on iron and nickel is used, the nickel content is less than 20% by weight and preferably less than 15%.

Prior to the chlorination reaction, the catalyst may be conditioned, if necessary, by a heat treatment in the presence of $Cl_2$ and/or HF, for example according to the method described in EP-B-0 609 124.

As has been mentioned, the process in accordance with the invention consists especially in placing chlorine in contact with F133a, in the presence of HF and a catalyst, under conditions such that HF does not substantially react with the F133a and the F123 formed to give more fluorinated derivatives. These conditions are advantageously chosen within the temperature, molar ratio and contact time zones indicated previously, and it will fall to a person skilled in the art to select the exact conditions of a reaction, taking into account the desired result. Thus, once the temperature parameter has been chosen, for example 280° C., it may be advantageous to reduce the $Cl_2$/F133a molar ratio, for example to about 10% in order to obtain the best selectivity towards 120 series at the expense of the 110 series. Similarly, for a certain temperature and a certain chlorine content, it will be convenient to choose the contact time that makes it possible to combine a suitable degree of conversion of the F133a and a good selectivity towards F123. Similarly also, the HF/F133a molar ratio may be chosen, for example, as a function of the desired or acceptable values for the 110 series/120 series molar ratio. As mentioned, this HF/F133a ratio may generally range from 0.5 to 2.5 taking into account the other reaction conditions (temperature, contact time, $Cl_2$/F133a molar ratio), but, preferably, this HF/F133a molar ratio is in the region of 1, for example between 0.8 and 1.2.

The preceding indications demonstrate that the values recommended for the operating conditions have an essentially informative role, given that it would not constitute a departure from the context of the invention to select, for any one of the reaction parameters, values lying above or below the values indicated previously, provided that such operating modifications do not involve a reaction of HF with F133a leading to the formation of substantial amounts of more fluorinated derivatives.

The chlorination reaction may be performed in the gas phase, in a fixed bed or in a fluid bed, batchwise or, preferably, continuously, with the possibility of recycling the unconverted reagents and the HF into the reactor. The hydrochloric acid formed during the reaction is preferably separated out before recycling. The F123 recovered may be purified by distillation according to the desired purity.

The chlorine may be introduced into the reactor in pure form or diluted in an inert gas such as nitrogen. The materials used for the construction of the plant must be compatible with the presence of chlorine and hydracids such as HCl and HF; they may be chosen, for example, from "Hastelloy" or "Inconel" which are resistant to corrosive media containing these hydracids.

The chlorination reaction according to the invention may be performed at atmospheric pressure or at a pressure above atmospheric pressure. For practical reasons, the process is generally performed in a region ranging from 0 to 25 bar relative and preferably between 0 and 15 bar relative.

Under operating conditions liable to foul the catalyst, it may be prudent to introduce oxygen in low content with the reagents. This content may vary according to the operating conditions between 0.02% and 5% relative to the organic reagents (molar percentage). The oxygen may be introduced continuously or sequentially.

The process in accordance with the invention allows the preparation of F123 from F133a, under moderate temperature and pressure conditions, with an excellent selectivity towards F123.

The starting 1,1,1-trifluoro-2-chloroethane (F133a) may itself be obtained by applying processes that are now well known. The F133a may especially be prepared by fluorinating trichloroethylene (for example according to the method recommended by McBee et al., Ind. Eng. Chem. 39, 409–412), by fluorinating F132b, by fluorinating F130a, by hydrogenolysing F113a or by fluorinating F1122 ($CF_2$=CHCl).

In the invention, preference is given to F133a obtained by fluorinating trichloroethylene.

In this respect, a subject of the invention is also a process for preparing F123 from trichloroethylene, the said process comprising:

a) a step of fluorinating trichloroethylene, in a reaction, in the liquid phase or in the gas phase, in the presence of a catalyst and at a pressure leading, after separating out HCl and the heavy fractions, to a mixture of F133a accompanied by HF entrained in azeotropic form;

b) a step of chlorinating F133a, by placing the said F133a in contact with chlorine, in the presence of HF and a catalyst, under temperature conditions, with a contact time and with $Cl_2$/F133a and HF/F133a ratios such that HF does not substantially react with the F133a and the F123 formed.

In phase a) for a liquid-phase process, a catalyst based on antimony salts is preferably used and the process is advantageously performed at a pressure of at least 10 bar absolute. The trichloroethylene may also be reacted with HF in the presence of chromium oxide or chromium oxyfluoride in a gas-phase process.

The F123 may be used in unmodified form, for example as a refrigeration propellant and in the manufacture of foams, in which it advantageously replaces F11 on account of its harmlessness with respect to the ozone in the stratosphere. As a result, the process in accordance with the invention, which, by virtue of the results it gives, may be exploited industrially, is particularly advantageous, starting either with trichloroethylene or with F133a.

The F123 may also undergo additional fluorination and thus give F125 (pentafluoroethane) This reaction may be performed according to various processes that are now known: in general, this step involves placing F123 (alone or as a mixture with other compounds of the 120 series) in contact with HF in the presence of a fluorination catalyst to obtain F125.

This step may be performed in the vapour phase, and the catalyst may be chosen from the catalysts whose use is described, for example, in EP-B-609 124 or in the references quoted in the said patent, the said patent being incorporated herein especially for the conditions recommended for this reaction.

A subject of the invention is thus also a process for preparing pentafluoroethane (F125), the said process comprising:
a) a step of fluorinating trichloroethylene as described above and resulting especially in F133a;
b) a step of chlorinating F133a, as described above and resulting especially in F123;
c) a step of fluorinating F123, by placing F123 in contact with HF, in the presence of a catalyst, with or without recycling of F124, the fluorination of F124 possibly being the subject of a separate step.

In this step, the catalyst is advantageously a mixed catalyst composed of oxides, halides and/or oxyhalides of nickel and of chromium as described in EP-B-609 124. Catalysts based on chromium oxide or oxyfluoride or based on alumina or aluminum fluoride, optionally doped with a metal such as zinc, nickel or iron, may also be used. Such catalysts are described, for example, in EP-502 605 or WO 93/16798. A catalyst of the chromium/charcoal type as described, for example, in EP-A-456 552 may also be used.

For this step, a mixed catalyst described above deposited on a support consisting of aluminum fluoride or a mixture of aluminum fluoride and alumina is preferably used.

The temperature of this fluorination reaction may be between 250 and 470° C. and is preferably between 280 and 410° C. The contact time between HF and F123 may be between 3 and 100 s and preferably between 5 and 30 s. The HF/F123 molar ratio may range from 1/1 to 20/1 and preferably from 2/1 to 9/1.

Although the reaction may be performed at atmospheric pressure, it is preferred to work under a slight pressure, for example not exceeding 10 bar absolute, or even less than 5 bar absolute.

The F125 obtained may then be purified, for example by applying the methods described in FR-2 758 137 or WO 95/21147, the content of which is incorporated herein by reference.

BRIEF DESCRIPTION OF THE DRAWINGS

The process for preparing F125 from trichloroethylene, which also constitutes a subject of the invention, may be carried out continuously in a plant as shown schematically by any one of the attached figures.

These figures illustrate an assembly scheme for the three Steps I, II and III of the process under consideration.

Figure 1:
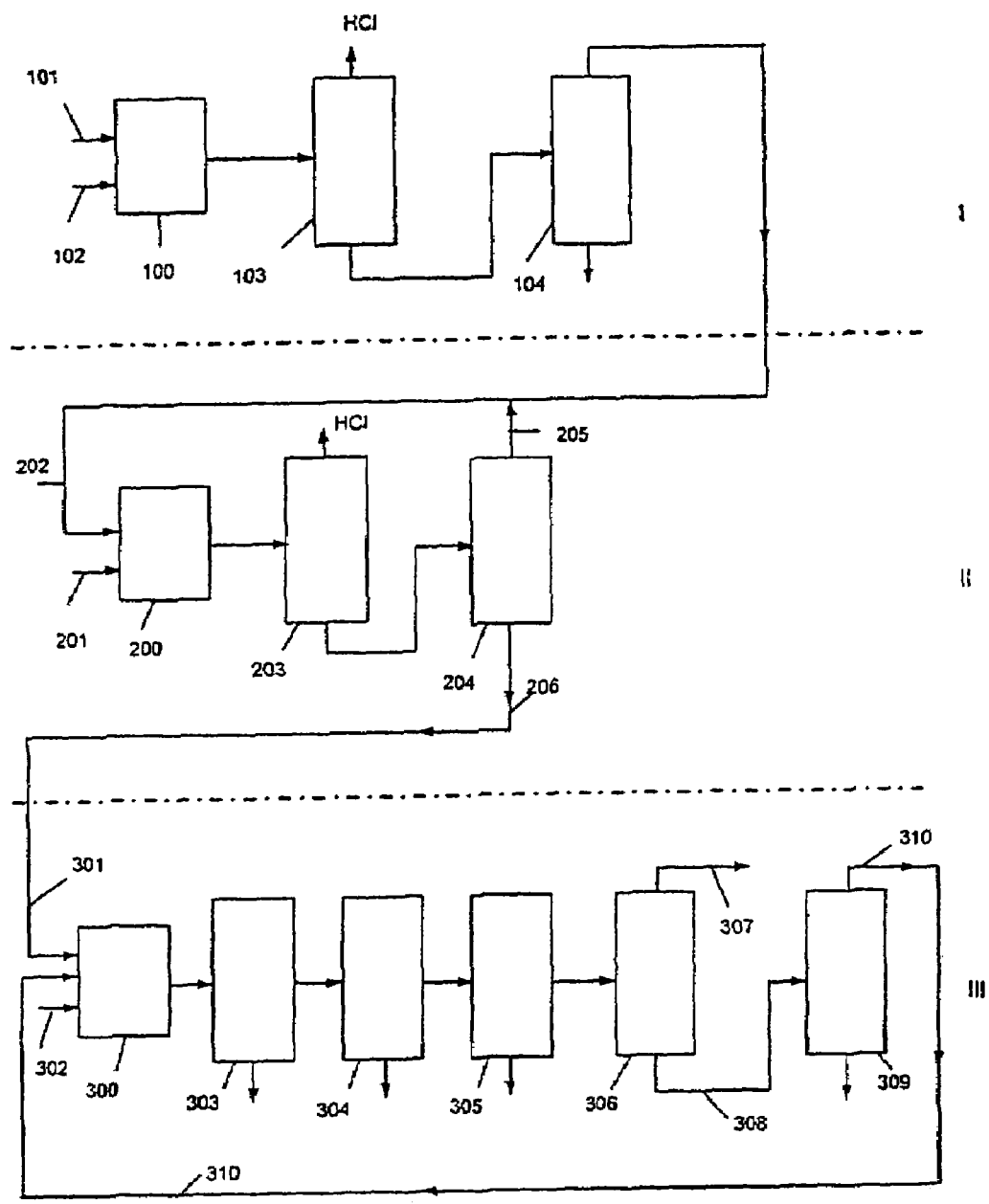

The plant especially comprises (see FIG. 1):
Step I
a reactor (100) containing the catalyst;
inlets for trichloroethylene (101) and HF (102);
an HCl distillation column (103);
a column for separating out F133a+HF from the heavy fractions (104):
Step II
a chlorination reactor (200) fed with:
F133a and HF (202);
chlorine (201);
an HCl separation column (203);
a column (204) for separating the crude F123 (206) from the unreacted F133a (+especially azeotropic HF+unreacted $Cl_2$) which are recycled (205);
a means for withdrawing the excess HF.
Step III
a fluorination reactor (300), fed with crude F123 (206/301) originating from column (204) from the preceding step, with HF (302) and optionally with crude F124 (310) recycled from column (309);
at the outlet of reactor (300), the devices for processing the reaction gases (columns 303, 304 and 305) intended to recover the HCl formed as byproduct by the reaction and the unconverted HF, and to neutralize the fluorocarbon compounds before distilling them;
a column (306) for then extracting as the head fraction the F125 (307), the tail fraction (308) then being distilled off on the column (309) to give a mixture F124+F123 (310) purified of its content of heavy fractions, the said mixture then being recycled into the reaction (300) to be fluorinated therein into F125.

Figure 2:
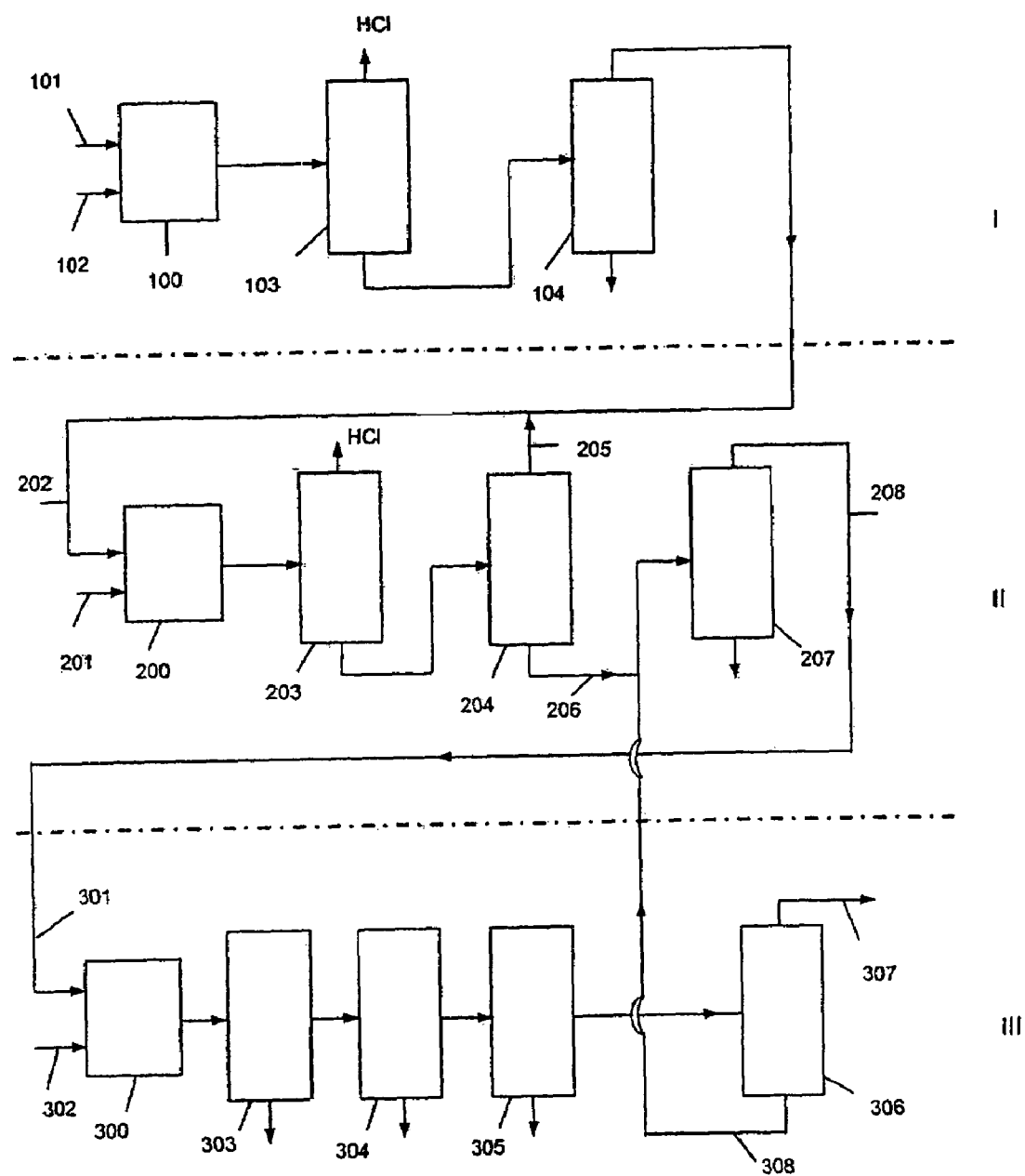

An advantageous option of this scheme is represented in FIG. 2, in which there is a column (207) for purifying both the crude F123 (206) derived from column (204) of Step II and the crude mixture F124+F123 derived from the tail fraction of column (306) of Step III: in this option, which allows the reaction (300) to be fed with cleaner products, the column (309) no longer needs to exist.

Needless to say, the industrial plant comprises additional devices that are commonly used (purge, evaporators, superheater, decanters).

The invention also relates to a plant for producing F125 from trichloroethylene, and which comprises at least the succession of devices as represented in the figure.

EXAMPLES

The invention will now be illustrated by the following examples, which are given purely for indicative purposes.

Example 1

Preparation of F123 by chlorination of F133a in the presence of HF and an iron-based catalyst.

75 $cm^3$ of a catalyst based on iron deposited on fluoroalumina, having an Fe content of 12% by weight, are introduced into an Inconel tube with an inside diameter of 21 mm.

The HF flow rate is adjusted to 0.91 mol/h and the temperature to 270° C. Next, a $Cl_2/N_2$ mixture containing 15 mol % of chlorine is introduced into the reactor at a flow rate of 0.91 mol/h. Finally, $CF_3$—$CH_2Cl$ is introduced into the reactor at a flow rate of 0.90 mol/h and the total reaction pressure is adjusted to 15 bar.

After reaction for 24 h, a gaseous sample is taken for analysis by gas chromatography. Another sample is taken after having removed the HF and chlorine from the flow derived from the reactor by sparging in wash bottles with water and sodium hydroxide/sulphite and then after having dried it over $CaCl_2$. It is similarly analysed by gas chromatography.

The conversion of F133a is 7.3% for a selectivity towards F123 of 96.9%. The 110 series/120 series ratio is 2.9%.

Examples 2 to 4

Preparation of F123 by chlorinating F133a in the presence of HF and an iron-based catalyst.

According to the same protocol as in Example 1, various conditions were tested. The test conditions and results obtained are collated in the table below:

|  | Example 2 | Example 3 | Example 4 |
|---|---|---|---|
| Conditions |  |  |  |
| Temperature (° C.) | 270 | 280 | 280 |
| MR $Cl_2$/F133a | 0.25 | 0.15 | 0.25 |
| MR HF/F133a | 1.1 | 1.1 | 1.2 |
| Tc(s) | 27 | 32 | 27 |
| Results |  |  |  |
| Conversion F133a % | 9.0 | 9.4 | 12.6 |
| Selectivity towards F123 % | 96.4 | 94.8 | 93.7 |
| 110/120 series ratio % | 3.4 | 3.9 | 5.7 |

Examples 5 to 7

Preparation of F123 by chlorinating F133a in the presence of HF and fluoroalumina as catalyst.

According to the same protocol as in Example 1, but replacing the catalyst with a fluoroalumina, various conditions were tested.

The test conditions and results obtained are collated in the table below:

|  | Example 5 | Example 6 | Example 7 |
|---|---|---|---|
| Conditions |  |  |  |
| Temperature (° C.) | 270 | 280 | 280 |
| MR $Cl_2$/F133a | 0.23 | 0.18 | 0.27 |
| MR HF/F133a | 1.0 | 1.2 | 1.0 |
| Tc(s) | 26 | 35 | 29 |
| Results |  |  |  |
| Conversion F133a % | 7.9 | 10.2 | 11.9 |
| Selectivity towards F123 % | 98.4 | 95.9 | 96.4 |
| 110/120 series ratio % | 1.6 | 4.1 | 3.4 |

Example 8 (Comparative)

Preparation of F123 by chlorinating F133a in the presence of fluoroalumina as catalyst and without HF.

75 cm³ of catalyst (fluoroalumina) are introduced into an Inconel tube with an inside diameter of 21 mm. The catalyst is treated for 15 h with 1 mol/h of anhydrous HF at 350° C. and atmospheric pressure.

Prior to the reaction, the HF flow is stopped, the temperature is reduced to 280° C. and a flow rate of nitrogen of 1.02 mol/h is introduced into the reactor. Next, a $Cl_2$/$N_2$ mixture containing 15 mol % chlorine is introduced into the reactor at a flow rate of 1.02 mol/h. Finally, $CF_3$—$CH_2Cl$ is introduced into the reactor at a flow rate of 1.1 mol/h and the total reaction pressure is adjusted to 15 bar.

After reaction for 24 h, a gaseous sample is taken for analysis by gas chromatography. Another sample is taken after having removed the HF and chlorine from the flow derived from the reactor by sparging in wash bottles containing water and sodium hydroxide/sulphite and then after drying it over $CaCl_2$. It is similarly analysed by gas chromatography.

The conversion of F133a is 9.5% for a selectivity towards F123 of 76.7%. The 110 series/120 series ratio is 23.5%.

Example 9 (Comparative)

Preparation of F123 by chlorinating F133a in the presence of fluoroalumina as catalyst and without HF:

A test was performed according to the same protocol as in Example 9, but under the following conditions: temperature=280° C., $CL_2$/F133a molar ratio=0.27, $N_2$/F133a molar ratio=1, contact time=23 s.

The conversion of the F133a is then 17%, for a selectivity towards F123 of 53%. The 110 series/120 series ratio is 70%.

Example 10 (Comparative)

Preparation of F123 by chlorinating F133a without HF and without a catalyst.

A flow rate of nitrogen of 0.94 mol/h is introduced into an empty Inconel tube with an inside diameter of 21 mm heated to 280° C., along with a $Cl_2$/$N_2$ mixture containing 15 mol % of chlorine at a flow rate of 0.95 mol/h. Finally, $CF_3$—$CH_2Cl$ is introduced into the reactor at a flow rate of 0.88 mol/h and the total reaction pressure is adjusted to 15 bar.

After reaction for 24 h, a gaseous sample is taken for analysis by gas chromatography. Another sample is taken after having removed the HF and chlorine from the flow derived from the reactor by sparging in wash bottles containing water and sodium hydroxide/sulphite and then after having dried it over $CaCl_2$. It is similarly analysed by gas chromatography.

The conversion of the F133a is 2.5% for a selectivity towards F123 of 91%.

The 110 series/120 series ratio is 8.5%.

Example 11 (Comparative)

Preparation of F123 by chlorinating F133a without HF and without a catalyst.

A test was performed according to the same protocol as in Example 15, but under the following conditions: temperature=280° C., $Cl_2$/F133a molar ratio=0.25, $N_2$/F133a molar ratio=1, flow rate of F133a=0.93 mol/h.

The conversion of the F133a is then 2.8%, for a selectivity towards F123 of 87%. The 110 series/120 series ratio is 13%.

Example 12 (Comparative)

Preparation of F123 by chlorinating F133a in the presence of HF and an Ni—Cr catalyst supported on fluoroalumina.

75 cm³ of Ni—Cr catalyst supported on fluoroalumina, with an Ni content of 6% by weight and a Cr content of 6% by weight (prepared as described in patent FR 2 669 022), are introduced into an Inconel tube with an inside diameter of 21 mm. The catalyst is treated for 15 h with 1 mol/h of anhydrous HF at 350° C. and atmospheric pressure.

Prior to the reaction, the HF flow rate is adjusted to 1.2 mol/h and the temperature to 280° C. Next, a $Cl_2$/$N_2$ mixture containing 15 mol % of chlorine is introduced into the reactor at a flow rate of 1.56 mol/h. Finally, $CF_3$—$CH_2Cl$ is introduced into the reactor at a flow rate of 1.18 mol/h and the total reaction pressure is adjusted to 15 bar.

After reaction for 24 h, a gaseous sample is taken for analysis by gas chromatography. Another sample is taken after having removed the HF and chlorine from the flow derived from the reactor by sparging in wash bottles containing water and sodium hydroxide/sulphite and then after having dried it over $CaCl_2$. It is similarly analysed by gas chromatography.

The conversion of the F133a is 12.8% for a selectivity towards F123 of 75.3%. The 110 series/120 series ratio is 8.2%.

Examples 13 and 14 (Comparative)

Preparation of F123 by chlorinating F133a in the presence of HF and an Ni—Cr catalyst supported on fluoroalumina.

According to the same protocol as in Example 13, various conditions were tested. The results are given in the table below:

|  | Example 13 | Example 14 |
| --- | --- | --- |
| Conditions |  |  |
| Temperature (° C.) | 270 | 280 |
| MR $Cl_2$/F133a | 0.28 | 0.28 |
| MR HF/F133a | 1.0 | 0.9 |
| Tc(s) | 32 | 31 |
| Results |  |  |
| Conversion F133a % | 16.9 | 21 |
| Selectivity towards F123 % | 73.7 | 74 |
| 110/120 series ratio % | 13.1 | 12.9 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

The invention claimed is:

1. Process for preparing pentafluoroethane (F125) comprising first preparing F123 by placing 1,1,1-trifluoro-2-chloroethane (F133a) in contact with chlorine, said process being performed:

in the presence of HF;

under temperature conditions, with a contact time and with $Cl_2$/F133a and HF/F133a molar ratios wherein HF substantially does not react with the F133a and the F123 formed, and promotes selectivity towards F123; and in the presence of a bulk catalyst consisting of aluminum fluoride or of a mixture of aluminum fluoride and alumina, or of a catalyst based on iron, or on iron and nickel, supported on aluminum fluoride or on a mixture of aluminum fluoride and alumina and fluorinating the produced F123 to obtain F125.

2. Process according to claim 1, in which the F123 is placed in contact with HF in the presence of a catalyst consisting of aluminum fluoride or of a mixture of aluminum fluoride and alumina, or of a catalyst based on iron, or on iron and nickel, supported on aluminum fluoride or on a mixture of aluminum fluoride and alumina.

3. Process according to claim 1, wherein the starting F133a is obtained by fluorination of trichloroethylene or by fluorination of trichloroethylene is performed in the liquid phase under pressure, in the presence of a catalyst based on antimony salts or in the gaseous phase in the presence of a catalyst based on chromium oxide or chromium oxyfluoride, said process comprising:

1) fluorinating trichloroethylene to F133a,
2) chlorinating F133a to F123,
3) fluorinating F123 to F125.

* * * * *